US009810655B2

(12) United States Patent
Park et al.

(10) Patent No.: US 9,810,655 B2
(45) Date of Patent: Nov. 7, 2017

(54) HYDROGEN ION ELECTRODE COMPOSED OF COMPOSITE MATERIAL OF NANO IRIDIUM OXIDE AND POLYMER RESIN AND ENABLING SURFACE REGENERATION, PH SENSOR USING SAME, AND METHOD FOR MANUFACTURING SAME

(71) Applicant: EZ SENSING INC., Seoul (KR)

(72) Inventors: Jong Man Park, Seongnam-si (KR); Moonhee Kim, Seoul (KR)

(73) Assignee: EZ SENSING INC., Seoul (KR)

( * ) Notice: Subject to any disclaimer, the term of this patent is extended or adjusted under 35 U.S.C. 154(b) by 91 days.

(21) Appl. No.: 14/911,558

(22) PCT Filed: Aug. 14, 2014

(86) PCT No.: PCT/KR2014/007578
§ 371 (c)(1),
(2) Date: Feb. 11, 2016

(87) PCT Pub. No.: WO2015/026104
PCT Pub. Date: Feb. 26, 2015

(65) Prior Publication Data
US 2016/0187281 A1    Jun. 30, 2016

(30) Foreign Application Priority Data

Aug. 20, 2013 (KR) .................. 10-2013-0098696
Aug. 13, 2014 (KR) .................. 10-2014-0105436

(51) Int. Cl.
*G01N 27/333* (2006.01)
*G01N 27/30* (2006.01)
(Continued)

(52) U.S. Cl.
CPC ............. *G01N 27/302* (2013.01); *B82B 3/00* (2013.01); *B29C 35/00* (2013.01); *B29C 39/02* (2013.01);
(Continued)

(58) Field of Classification Search
CPC ............. G10N 27/333; G10N 27/3335; G10N 27/302; B29C 2059/027; B29C 43/00;
(Continued)

(56) References Cited

U.S. PATENT DOCUMENTS 5,624,977 A * 4/1997 Takarada ............... C08G 77/24
428/402.21

FOREIGN PATENT DOCUMENTS

KR   10-2004-0023169   3/2004
KR   10-2006-0084264   7/2006
(Continued)

OTHER PUBLICATIONS

Korean Intellectual Property Office computer-generated English language translation of Yoon et al. KR 10-2006-0029173.*
(Continued)

*Primary Examiner* — Alexander Noguerola
(74) *Attorney, Agent, or Firm* — Stein IP, LLC

(57) ABSTRACT

Provided are a hydrogen ion electrode composed of a composite material of polymer resin and nano iridium oxide, the composite material containing 1-10 nm sized nano iridium oxide particles and/or aggregates thereof which are dispersed to be electrically connected to each other in a moldable, thermoplastic, and hydrophobic polymer resin matrix; a pH sensor using the same; and a method for manufacturing the same. The surface of the hydrogen ion electrode shows very fast pH sensitivity when exposed to a sample solution, and the pH sensitivity is approximate to biphasic characteristics. Furthermore, regardless of high reproducibility of pH sensitivity, abrupt pH change, and repetitive use, very low hysteresis, durability due to high physical strength, and high surface regeneration due to polishing are exhibited, and thus, the lifetime of the elec-
(Continued)

trode can be extended and various sizes and shapes of electrodes can be easily manufactured.

14 Claims, 9 Drawing Sheets

(51) Int. Cl.
*B82B 3/00* (2006.01)
*B29C 59/02* (2006.01)
*C08J 3/24* (2006.01)
*B29C 35/00* (2006.01)
*B29C 39/02* (2006.01)
*B82Y 15/00* (2011.01)
*B82Y 30/00* (2011.01)
*B82Y 40/00* (2011.01)
*G01N 27/416* (2006.01)

(52) U.S. Cl.
CPC ......... *B29C 2059/027* (2013.01); *B82Y 15/00* (2013.01); *B82Y 30/00* (2013.01); *B82Y 40/00* (2013.01); *C08J 3/24* (2013.01); *G01N 27/4167* (2013.01)

(58) Field of Classification Search
CPC ..... B29C 43/003; B29C 43/006; B29C 35/00; B29C 35/02; B29C 29/00; B29C 29/006; B29C 29/02
See application file for complete search history.

(56) References Cited

FOREIGN PATENT DOCUMENTS

| KR | 10-2006-0029173 | * | 8/2007 | ............. G01N 35/00 |
| KR | 10-0776981 | | 11/2007 | |

OTHER PUBLICATIONS

Fog A., "Electronic Semiconducting Oxides, as pH Sensors", *Sensors and Actuators* 5:137-146 (1984).
Jun H.M., "Electroananlytical Characteristics of IrO$_2$ Microparticle-Modified and Silver Nanoparticle-Modified Polymeric Composite Electrodes", *Konkuk University doctorate thesis*, see pp. 14-43 (Feb. 2010).
Midgley D., "A Review of pH Measurement at High Temperatures", *Talanta* 37(8):767-781 (1990).
Park J. et al., "A Surface Renewable Iridium Oxide-Glass Composite Hydrogen Ion Electrode", *Microchemical Journal* 95:102-106 (2010).
Quan H. et al., "Surface Renewable Hydrogen Ion-Selective Polymeric Composite Electrode Containing Iridium Oxide", *Bull. Korean Chem. Soc.* 26(10):1565-1568 (2005).
Vanhoudt P. et al., "Iridium Oxide pH Microelectrode", *Biotechnology and Bioengineering* 40:601-608 (1992).
International Search Report dated Nov. 24, 2014 received in International Application No. PCT/KR2014/007578.

* cited by examiner

[Fig. 1]
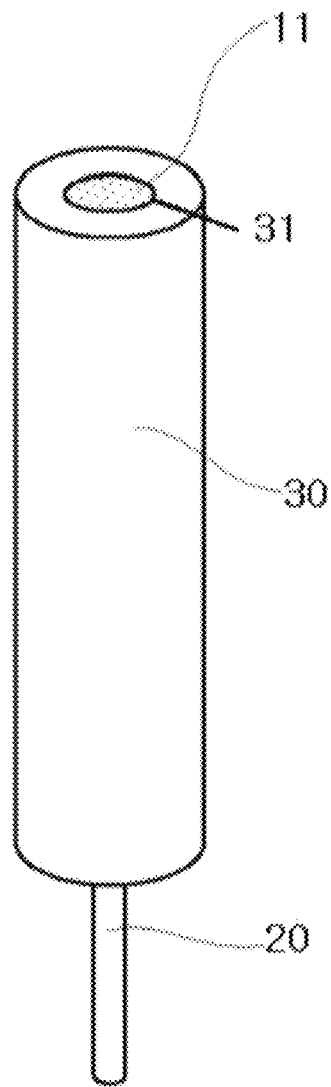

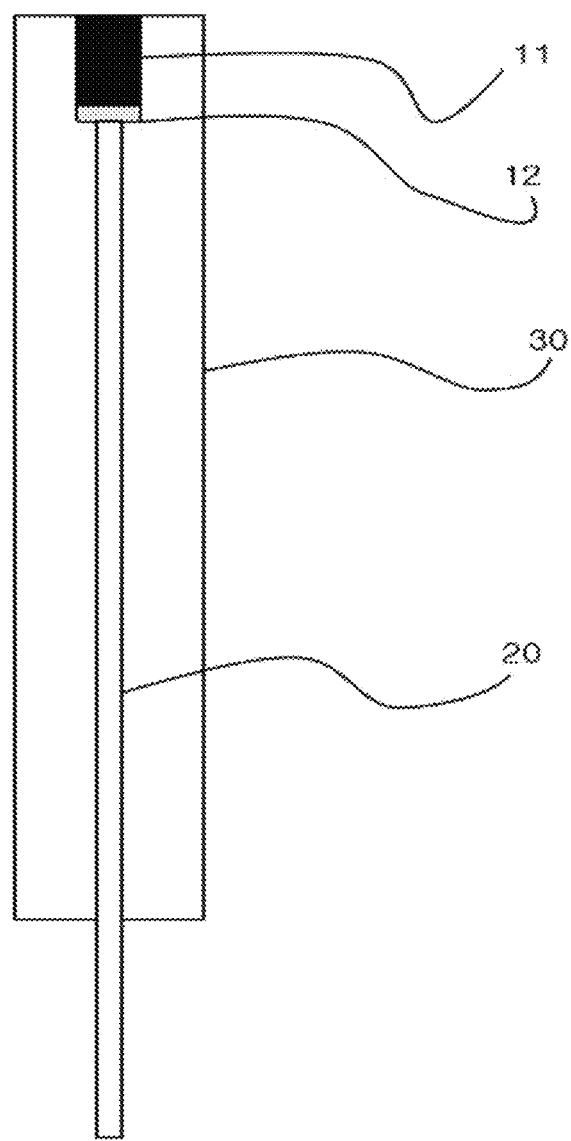
[Fig. 2]

[Fig. 3]
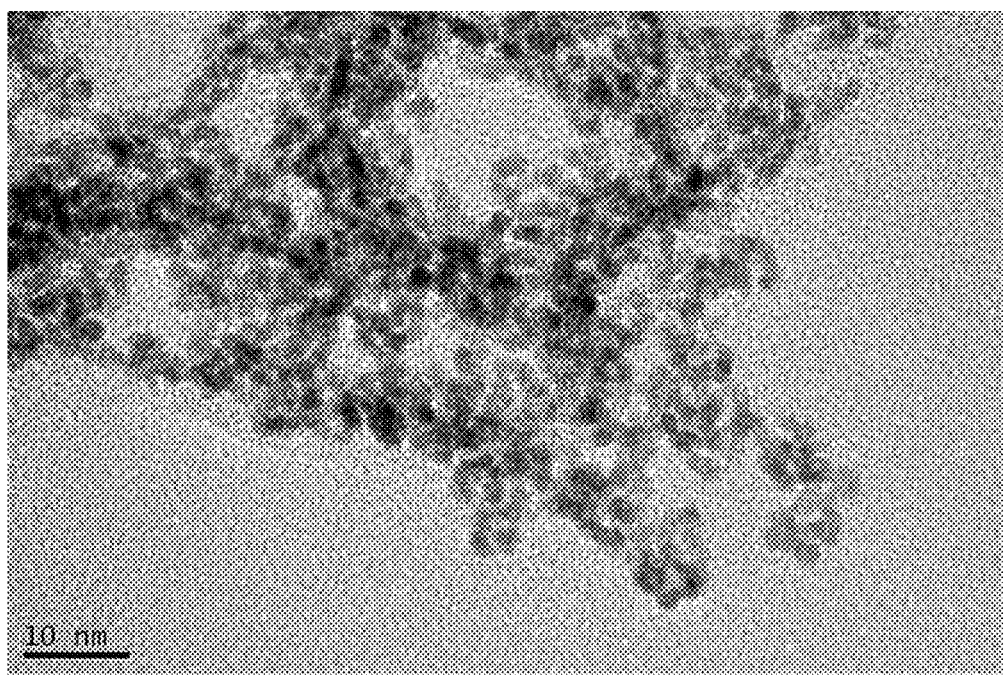

[Fig. 4]
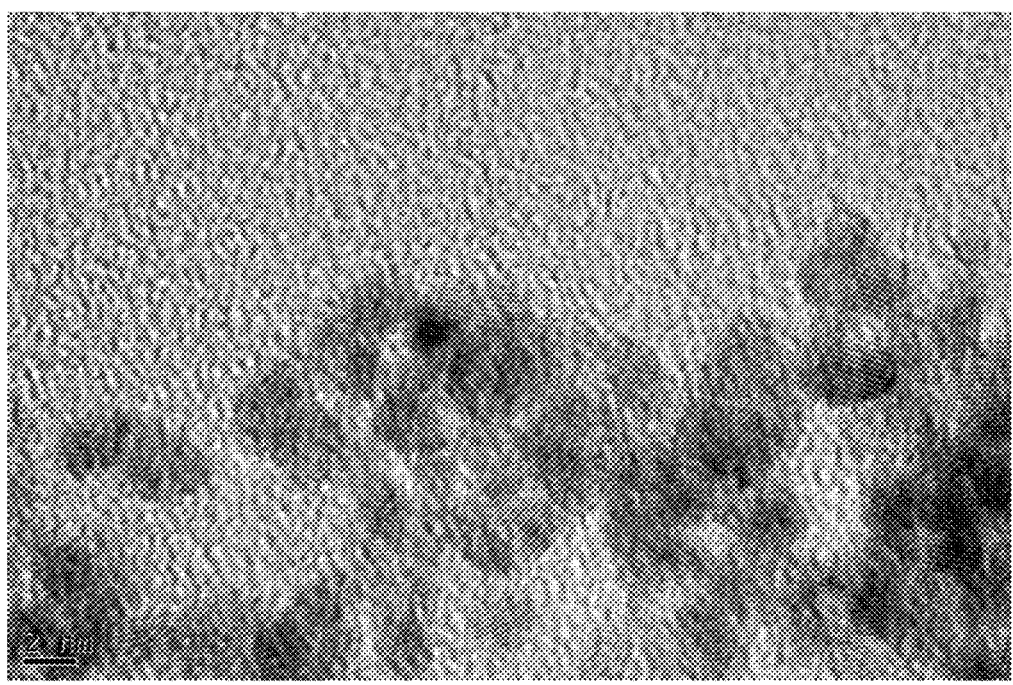

[Fig. 5]
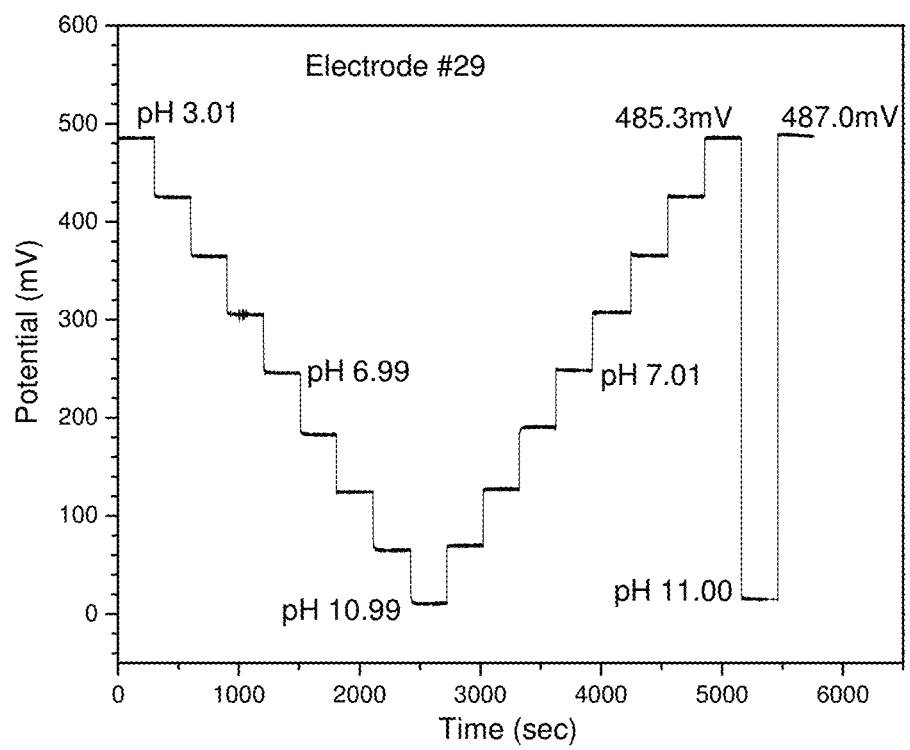

[Fig. 6]
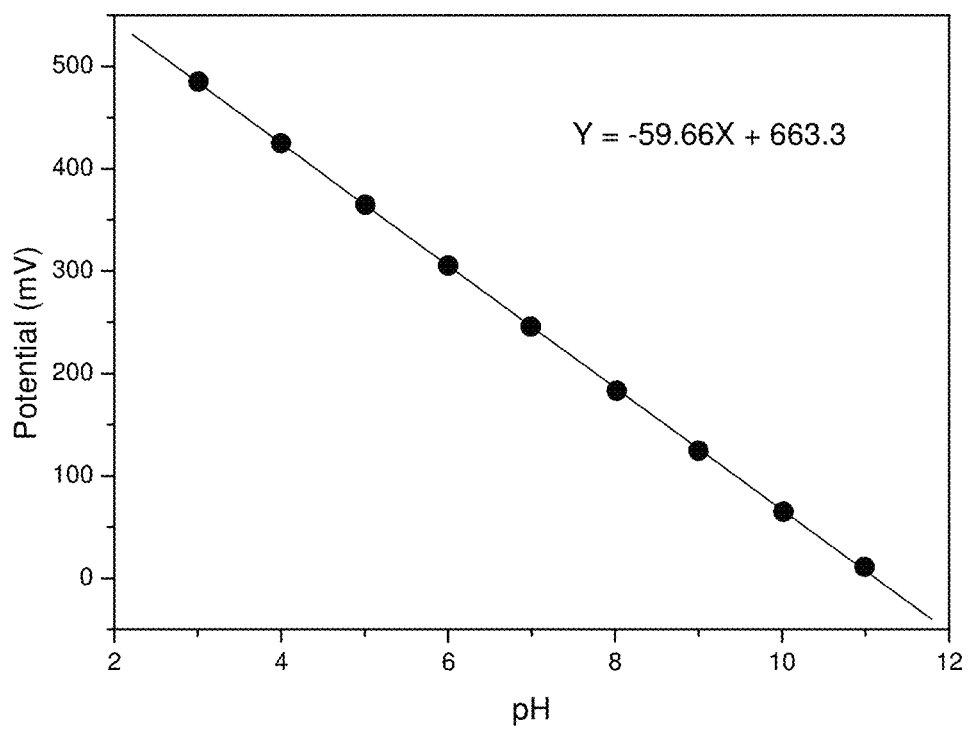

[Fig. 7]
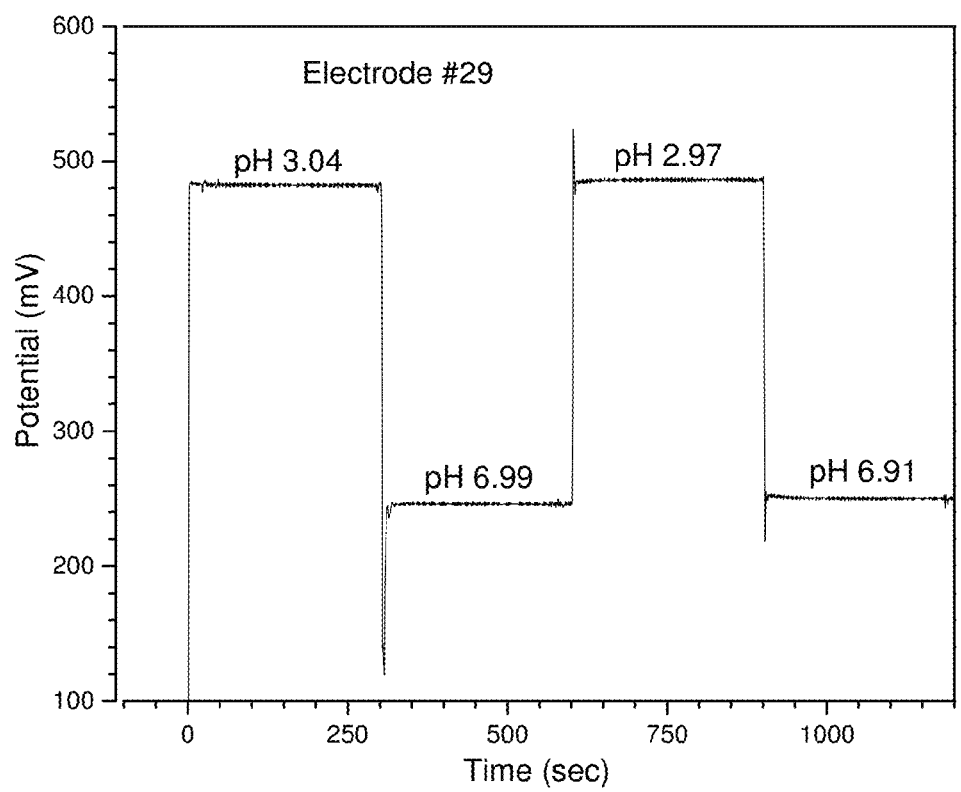

[Fig. 8]
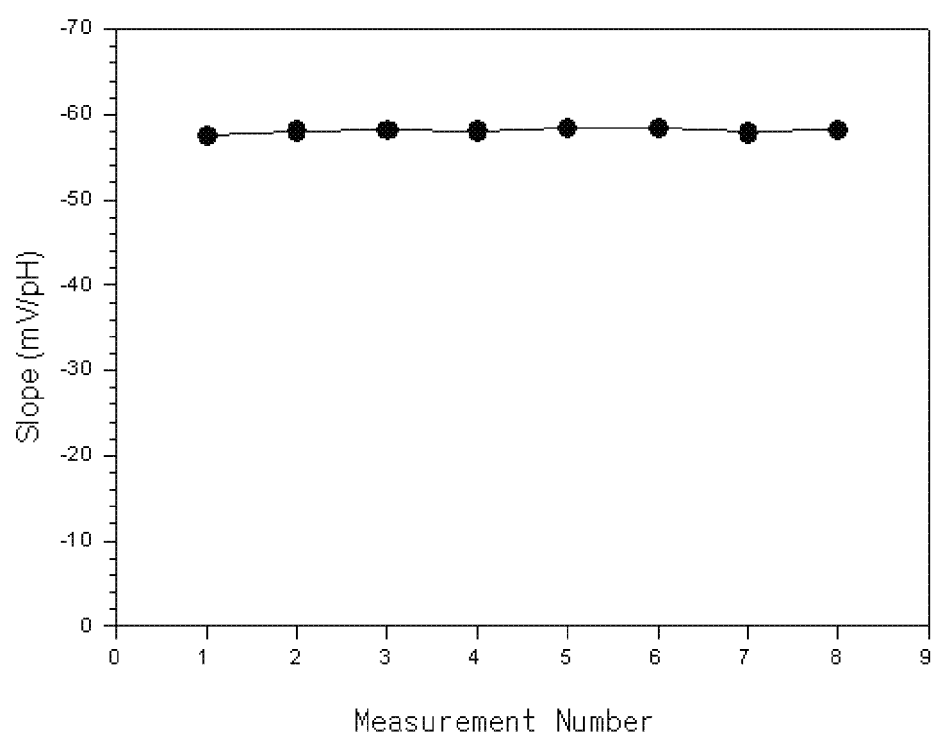

[Fig. 9]
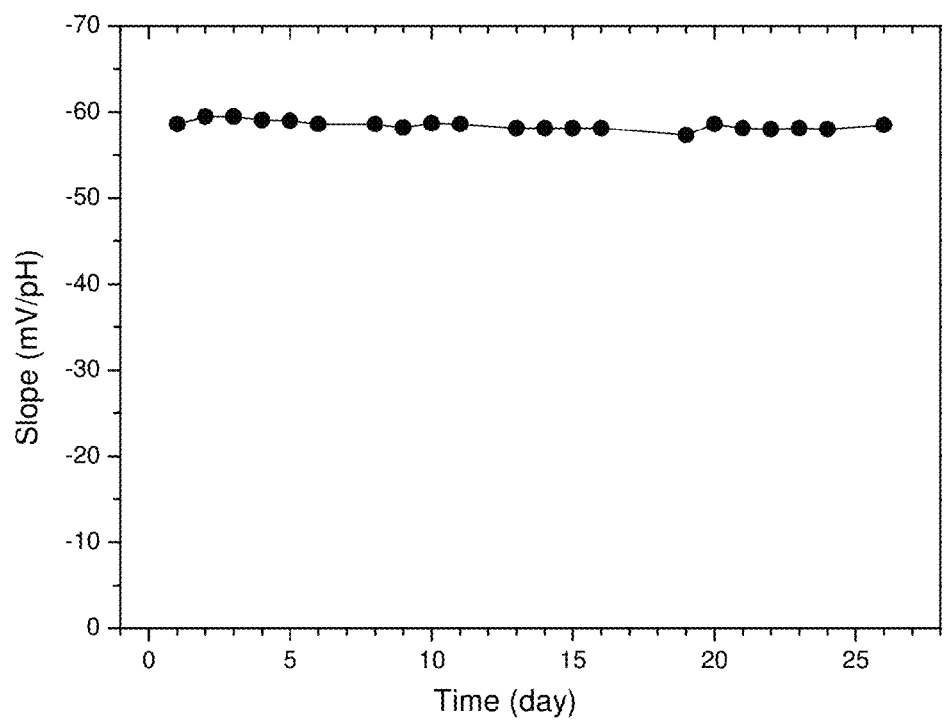

US 9,810,655 B2

HYDROGEN ION ELECTRODE COMPOSED OF COMPOSITE MATERIAL OF NANO IRIDIUM OXIDE AND POLYMER RESIN AND ENABLING SURFACE REGENERATION, PH SENSOR USING SAME, AND METHOD FOR MANUFACTURING SAME

TECHNICAL FIELD

This invention relates to a hydrogen ion electrode composed of a composite material of nano iridium oxide and a polymer resin and enabling surface regeneration by surface polishing, a pH sensor using the same, and a method for manufacturing the same.

BACKGROUND ART

As one of the basic analysis parameters used in various fields related to the environment, food, medicine, pharmaceuticals, etc., pH is used, and to measure this, a pH sensor is used.

As a conventional pH sensor, a pH-selective glass membrane electrode has been generally used. However, the electrode is fragile, and difficult to be activated when fouled.

That is, for examples, as a water quality monitoring system is operated for a long period, the sensor is exposed to an environmental sample for long period, or severe fouling on a surface of the sensor is caused due to the properties of the samples in soil analysis, a food process, etc. Consequently, as well as deactivation of the pH sensor caused thereby, severe fouling is caused. For this reason, the sensor has to be periodically replaced or activated.

Metal oxide films formed on the surface of the metal electrodes may be used to measure the concentration of hydrogen ions because the redox potentials of the oxides are dependent on the concentration of hydrogen ions. Such metal oxides may be $TiO_2$, $RuO_2$, $RhO_2$, $SnO_2$, $Ta_2O_5$, $OsO_2$, $PdO_2$, $PtO_2$ or $IrO_2$ (Non-patent document 1).

In the hydrogen ion-selective electrodes using metal oxides, reversible redox potentials of the metal oxides are dependent on the concentration of hydrogen ions. In the manufacturing of the metal oxide film pH electrodes, sputtering, high-temperature thermal decomposition or electrochemical oxidation of a metal wire are applied.

A typical electrochemical technique is an oxidizing method of iridium (Ir electrode to an iridium (IV) oxide, for example, by dipping an iridium (Ir) metal electrode in a sulfuric acid solution, and cycling the potential of the electrode between −0.25 and +1.25 V (vs. SCE) repeatedly. The iridium oxide formed on the surface of the metal electrode is known to be a hydrated iridium oxide in a form of $IrO_2.4H_2O$, $Ir(OH)_4.2H_2O$, and $[IrO_2(OH)_2.2H_2O]^{2-}$, and to have a super-Nernstian response of about −90 mV/pH unit (Non-patent document 2).

Also, in the case of iridium oxide film electrode prepared on the surface of platinum or iridium, or a conductive metal electrode by sputtering or thermal decomposition, the iridium oxide on its surface is known to be an anhydrous iridium oxide, and exhibits a sensitivity of about −59 mV/pH with respect to the concentration of hydrogen ions (Non-patent document 3).

Since the iridium oxide coated film is formed at high temperature or in a high vacuum environment, the iridium oxide coated film electrode manufactured by sputtering or thermal decomposition has microscopic uniformity of the coated film and micropores formed during the thermal decomposition, and therefore a permeation time of a solution is increased, resulting in a delayed sensing rate.

Also, when a measuring solution is changed, prompt and complete change of the solution in the coated film is difficult. Thus, there are problems of the delayed sensing time, low reproducibility, and a sensitivity slope deviating far from the theoretical sensitivity slope (−59.2 mV/pH). Also, when its surface is fouled, or the sensitivity of the electrode is degraded, it is not easy to regenerate the electrode properties effectively, resulting in a reduced lifetime of the electrode.

Recently, a modified glass or ceramic composite material electrode manufactured by mixing a conductive metal microparticle mixture with a glass or ceramic powder, molding the mixed product, and sintering the molded product at high temperature was reported (Non-patent document 4 and Patent document 1).

However, according to the research conducted by the inventors, the above-described technique has problems of low reproducibility of the electrode signal, low sensing rate due to the time needed for the surface equilibration, and a high hysteresis with respect to abrupt pH change, and since the electrode is manufactured by mixing, molding, and then sintering the glass or ceramic powder at high temperature, the electrode is difficult to be manufactured.

Meanwhile, a hydrogen ion electrode in which carbon black and iridium oxide particles were bound using polymer resin binder was reported (Non-patent document 5).

However, according to the research result by the inventors, although the hydrogen ion electrode has excellent physical stability and surface renewability, compared to the conventional glass electrode or polymer membrane electrode, the manufacturing process is complicated because it is necessary to add a conductor such as carbon black. Also, the pH dependency of the polymer electrode has a large variation in a range from 50 to 60 mV/pH by production lot. Also, a relatively high hysteresis of about 5 mV is observed when the pH is changed abruptly in wide range, and measured pHs have large errors of about 0.1 pH unit.

PRIOR ART DOCUMENTS

Patent Document (Patent document 1): Korean Patent No. 776981

Non-Patent Documents (Non-patent document 1): A. Fog, R. P. Buck, Sensors and Actuators, 1984, 5, 137-146
(Non-patent document 2): D. Midgly, Talanta, 1990, 37, 767-781
(Non-patent document 3): P. VanHoudt, Z. Lewandowski, B. Little, Biotech. Bioeng. 1992, 40, 601-608
(Non-patent document 4): J. Park, J. Kim, H. Quan, Microchem. J. 2010, 95, 102-106
(Non-patent document 5): H. Quan, W. Kim, K.-C. Chung, J. Park, Bull. Korean Chem. Soc. 2005, 26, 1565-1568

SUMMARY OF INVENTION

Technical Problem

In exemplary embodiments of the present invention, in one aspect, the present invention is directed to providing a hydrogen ion electrode composed of a composite material of nano iridium oxide and a polymer resin which is a pH electrode utilizing the electrical conductivity of the nano iridium oxide itself contained in the electrode composed of the composite material without an aid of a conductor, carbon black, and showing very fast response and near-theoretical pH sensitivity by the nano iridium particles on the surface of the electrode exposed to a solution [pH dependency close to the theoretical value (−59.2 mV/pH)], high reproducibility of the pH sensitivity, a very low hysteresis despite abrupt (wide range) pH change and repetitive use, durability in accordance with high physical strength, and high surface renewability.

In exemplary embodiments of the present invention, in another aspect, the present invention is directed to providing a pH sensor including the hydrogen ion electrode.

In exemplary embodiments of the present invention, in still another aspect, the present invention is directed to providing, unlike the conventional manufacturing methods, a method for manufacturing the above-described hydrogen ion electrode in a very simple manufacturing process.

Solution to Problem

Exemplary embodiments of the present invention provide a hydrogen ion electrode composed of a composite material of nano iridium oxide and a polymer resin, and enabling surface regeneration, in which the nano iridium oxide particles having a size of 1 to 10 nm are dispersed in a moldable, thermoplastic and hydrophobic polymer resin matrix in a state of individual particles, an aggregate state in which the particles agglomerate, or a state in which the individual particles and the aggregates are mixed. The nano iridium oxide particles are electrically connected in the matrix to allow electrical conduction of the hydrogen ion electrode.

In an exemplary embodiment, the nano iridium oxide particles having a size of 1 to 10 nm are dispersed in a state of individual particles, and the individual particles are electrically connected to allow the electrical conduction of the hydrogen ion electrode.

In an exemplary embodiment, the nano iridium oxide particles having a size of 1 to 10 nm are dispersed in an aggregate state in which the particles agglomerate, and the aggregates of the nano iridium oxide particles are electrically connected to allow the electrical conduction of the hydrogen ion electrode.

In an exemplary embodiment, the nano iridium oxide particles having a size of 1 to 10 nm are dispersed in a state in which the individual particles and aggregates are mixed, the nano iridium oxide particles or aggregates thereof are electrically connected to allow the electrical conduction of the hydrogen ion electrode.

In an exemplary embodiment, the hydrogen ion electrode contains 20 to 45 wt % of the nano iridium oxide particles and 80 to 55 wt % of the polymer resin.

In an exemplary embodiment, the hydrogen ion electrode may have a hysteresis potential of 1 to 2 mV according to abrupt (wide range) pH change in which the pH is increased from 3 to 11, and then decreased to 3.

In an exemplary embodiment, the polymer resin may be a polymer resin having a glass transition temperature ($T_g$) of 20° C. or higher, or a mixture thereof.

Exemplary embodiments of the present invention, in addition, provide a pH sensor including a non-electrically conductive housing, the hydrogen ion electrode located in the housing and an electrical contact means connected to the hydrogen ion electrode.

In an exemplary embodiment, the housing is a cylindrical housing, which has an open part exposing the electrode sensitive part at one side, and the electrical contact means connected to the outside of the housing at the other side.

Exemplary embodiments of the present invention, in addition, provide, as a method for manufacturing the hydrogen ion electrode, a method for manufacturing hydrogen ion electrode composed of a composite material of nano iridium oxide and a polymer resin, which includes preparing a mixed solution of one or more selected from the group consisting of a moldable, thermoplastic and hydrophobic polymer resin, nano iridium oxide particles having a size of 1 to 10 nm and aggregates in which the nano iridium oxide particles agglomerate, and a water-soluble organic solvent;

obtaining a composite material of a polymer resin and nano iridium oxide by adding water to the mixed solution and removing the water-soluble organic solvent; and manufacturing a hydrogen ion electrode by hot-molding the composite material.

In an exemplary embodiment, the manufacturing method further includes preparing the nano iridium oxide particles and/or aggregates thereof, and the nano iridium oxide particles and/or aggregates thereof are dispersed in the water-soluble organic solvent.

In an exemplary embodiment, in the manufacturing method, in the operation of preparing the mixed solution, after the polymer resin is dissolved in a water-soluble organic solvent to prepare a mixed solution, the nano iridium oxide particles and/or aggregates thereof may be mixed with and dispersed in the mixed solution.

In an exemplary embodiment, in the manufacturing method, in the operation of preparing the mixed solution, after the mixed solution is prepared by mixing and dispersing the nano iridium oxide particles and/or aggregates thereof in the water-soluble organic solvent, the polymer resin may be mixed with and dispersed in the mixed solution.

In an exemplary embodiment, in the manufacturing method, in the operation of preparing the mixed solution, the polymer resin is dissolved in a water-soluble organic solvent to prepare a first mixed solution, the nano iridium oxide particles and/or aggregates thereof are mixed with and dispersed in a water-soluble organic solvent to prepare a second mixed solution, and the first mixed solution and the second mixed solution may be mixed and dispersed.

In an exemplary embodiment, the polymer resin used in the manufacturing method may be a moldable, thermoplastic and hydrophobic polymer resin having a glass transition temperature of 20° C. or higher, or a mixture thereof, for example, a polymethylmethacrylate (PMMA) resin, a polyvinylchloride (PVC) resin, an acrylonitrile butadiene styrene (ABS) resin or a mixture thereof.

In an exemplary embodiment, the water-soluble organic solvent used in the manufacturing method may be acetone, tetrahydrofuran (THF), dimethylformamide (DMF) or dimethylsulfoxide (DMSO).

In an exemplary embodiment, in the manufacturing method, the composite material may be ground into powder, and then hot-molded.

In an exemplary embodiment, in the manufacturing method, a surface of the manufactured hydrogen ion electrode may be polished.

In an exemplary embodiment, in the manufacturing method, the surface of the manufactured hydrogen ion electrode may be polished, and stabilized in water (e.g., deionized water).

In an exemplary embodiment, the manufacturing method may further include binding the hot-molded hydrogen ion electrode into the non-electrically conductive housing, and connecting electrical contact means to the hydrogen ion electrode.

Advantageous Effects of Invention

The hydrogen ion electrode according to exemplary embodiments of the present invention can have a very fast and near-theoretical pH sensitivity by the nano iridium particles on the surface of the electrode exposed to a sample solution [pH dependency (e.g., −59.6 or −59.7 mV/pH, the correlation coefficient of 0.9999 or higher) close to the theoretical value (−59.2 mV/pH)], high reproducibility (e.g., reproducibility with relative errors of 0.4~0.5%), excellent surface renewability (e.g., surface renewability with relative errors of 0.4~0.5%), and a very low hysteresis of 1 to 2 mV despite abrupt (wide range) pH change and repetitive use.

Also, the hydrogen ion electrode according to exemplary embodiments of the present invention may have durability in accordance with high physical strength and high surface renewability as described above, and thus reproducible regeneration of the electrode surface can be possible through simple polishing when the electrode is fouled or deactivated.

Also, according to the manufacturing method of exemplary embodiments of the present invention, which is not a conventional complicated manufacturing method requiring a conductor such as carbon black, the hydrogen ion electrode can be manufactured in a very simple manufacturing process since the hydrogen ion electrode is formed of a matrix composed of a polymer composite material in which the nano iridium oxide particles are dispersed (individual particles are dispersed and/or aggregates thereof are dispersed).

The hydrogen ion electrode can be useful to detect the pH in water quality monitoring systems or on-line detecting systems, which monitor the concentration of hydrogen ions in a solution for a long period of time, or of a sample causing severe fouling on the sensor surface, for example, food, soil, waste, or bio-samples, while regenerating the surface by polishing.

BRIEF DESCRIPTION OF DRAWINGS

FIGS. 1 and 2 are schematic diagrams of a pH sensor including a hydrogen ion electrode according an exemplary embodiment of the present invention, where FIG. 1 is a schematic perspective view of the pH sensor and FIG. 2 is a schematic cross-sectional view of the pH sensor.

FIGS. 3 and 4 are transmission electron microscope (TEM) images of nano iridium oxide particles or aggregates thereof prepared in an example of the present invention, where FIG. 3 shows aggregates (scale bar: 10 nm), and FIG. 4 shows individual particles in an aggregate (scale bar: 2 nm).

FIG. 5 is a graph showing a potential change according to the pH change of a hydrogen ion electrode composed of a composite material of nano iridium oxide and a polymer resin in an example of the present invention (standard electrode: Ag/AgCl), where the X axis is time (sec) and the Y axis is an electric potential (mV).

FIG. 6 is a graph showing the dependency of an electrode potential according to the pH change of a hydrogen ion electrode composed of a composite material of nano iridium oxide and a polymer in an example of the present invention, where the X axis is pH, and the Y axis is an electric potential (mV).

FIG. 7 is a graph showing a response time versus the pH change of a hydrogen ion electrode composed of a composite material of nano iridium oxide and a polymer in an example of the present invention, where the X axis is time (sec), and the Y axis is an electric potential (mV).

FIG. 8 is a graph showing the reproducibility of a hydrogen ion sensitivity slope according to the polishing of a surface of a hydrogen ion electrode composed of a composite material of nano iridium oxide and a polymer according to an example of the present invention, where the X axis is a measurement number, and the Y axis is a hydrogen ion sensitivity slope (mV/pH).

FIG. 9 is a graph showing stability over time of a hydrogen ion sensitivity slope of a hydrogen ion electrode composed of a composite material of nano iridium oxide and a polymer in an example of the present invention, where the X axis is a measuring day and the Y axis is a hydrogen ion sensitivity slope (mV/pH).

EXPLANATION OF REFERENCE NUMERALS

11: hydrogen ion electrode 12: conductive adhesive part
20: electrical contact means 30: housing
31: open part

DETAILED DESCRIPTION OF EMBODIMENT

Hereinafter, the present invention will be described in detail with reference to exemplary embodiments of the present invention.

In the specification, iridium oxide is the common name of iridium oxide or hydrated iridium oxide ($IrO_y$ or $IrO_y \cdot nH_2O$; for reference, where y is 2 for a bulk composition, but cannot be specified for a nano oxide having particles with a very small size and a considerably large surface).

In the specification, the nano iridium oxide includes nano iridium oxide particles or aggregates thereof.

In the specification, the aggregates are formed by forming the nano iridium oxide particles in aggregation units which are differentiated from each other.

In exemplary embodiments of the present invention, as a hydrogen ion electrode in which nano iridium oxide particles having a size of 1 to 10 nm are dispersed in a moldable, thermoplastic and hydrophobic polymer resin matrix, a hydrogen ion electrode composed of a composite material of nano iridium oxide and a polymer resin and enabling surface regeneration is provided. Here, the nano iridium oxide particles are electrically connected in a matrix to allow electrical conduction of the hydrogen ion electrode.

In detail, the hydrogen ion electrode composed of the composite material of nano iridium oxide and a polymer resin and enabling surface regeneration according to exemplary embodiments of the present invention is a hydrogen ion electrode in which nano iridium oxide particles having a size of 1 to 10 nm are dispersed in the moldable, thermoplastic and hydrophobic polymer resin matrix (dispersed in a state of individual particles and/or an aggregate state in which corresponding particles partially agglomerate). Here, at least some or all of the nano iridium oxide particles dispersed in the polymer resin matrix and/or aggregates thereof are electrically connected in the polymer matrix to allow electrical conduction of the hydrogen ion electrode. It has been revealed that the structure in which the nano iridium oxide particles having a nano size of 1 to 10 nm and/or the aggregates thereof are dispersed to be electrically connected in the polymer matrix of the hydrogen ion electrode can provide significant advantages, compared to conventional hydrogen ion electrodes.

That is, for example, when the surface of the hydrogen ion electrode is regenerated by polishing (generally, in surface regeneration through polishing, sensitivity is reduced), in the surface-exposed hydrogen ion electrode, the nano iridium oxide particles having a size of 1 to 10 nm dispersed to be in contact and connected to allow electrical conduction in the polymer resin matrix and/or aggregates thereof (which become a hydrogen ion-sensitive material) may be immediately sensitive (instantly perform an equilibration reaction of pH sensitivity with the sample solution) to a sample solution, increase reproducibility of the immediate sensitivity, and decrease hysteresis despite repetitive use or abrupt pH change.

Also, since the polymer resin matrix in which the nano iridium oxide particles and/or aggregates thereof are dispersed has substantially few pores, almost little or no permeation of the sample solution through the pores occurs in the surface (the surface to be an electrode sensitive part), and thus the sample solution may be instantly in contact with the dispersed nano iridium oxide particles and/or aggregates thereof.

In an exemplary embodiment, the nano iridium oxide particles having a size of 1 to 10 nm are dispersed in the matrix in a state of individual particles and electrically in contact and connected (that is, forming a pathway of electrical conduction) to enable electrical conduction of the hydrogen ion electrode.

In an exemplary embodiment, the nano iridium oxide particles having a size of 1 to 10 nm may form a unit of an aggregate of the nano iridium oxide particles, and such aggregate units may be in contact and connected at least in some parts (forming the pathway of the electrical conduction) to enable the electrical conduction of the hydrogen ion electrode. Likewise, when the nano iridium oxide aggregate units in which the nano iridium oxide particles having a size of 1 to 10 nm agglomerate are dispersed in the polymer resin matrix, a large specific surface area to be in contact with the sample solution in the electrode sensitive part may be provided.

In an exemplary embodiment, the individual particles and the aggregates may be mixed, and the corresponding particles and/or aggregates are in contact and connected (forming the pathway of the electrical conduction) to allow the electrical conduction of the hydrogen ion electrode.

As described above, to achieve near-theoretical pH sensitivity, high reproducibility, excellent surface renewability, and low hysteresis, the composite material of the exemplary embodiments of the present invention may have the nano iridium oxide particles having a size of 1 to 10 nm, 2 to 10 nm, 2 to 5 nm, or 2 to 4 nm. Also, when the size of the nano iridium oxide particles is smaller than 1 nm, there is a difficulty in separation and filtration (collecting) of the nano iridium oxide particles, and when the size of the nano iridium oxide particles is larger than 10 nm, it may be difficult to prepare the composite electrode material, and the above-described properties of the electrode may be degraded. Also, in aspects of the preparation of the nano iridium oxide particles and the composite electrode material, and maintenance of the properties of the electrode, the size of the nano iridium oxide particles may be 2 to 10 nm, 2 to 5 nm or 2 to 4 nm.

In an exemplary embodiment, the hydrogen ion electrode has the nano iridium oxide aggregates dispersed in the polymer resin, and therefore may have a very low hysteresis of 1 to 2 mV despite abrupt (wide range) pH change in which pH is increased from 3 to 11 and then decreased to 3 or repetitive use. Such a hysteresis property is very superior to that of a conventional iridium oxide coating film electrode, or a composite electrode material of iridium oxide and glass or ceramic.

In an exemplary embodiment, the hydrogen ion electrode may contain 20 to 45 wt % of the nano iridium oxide particles having a size of 1 to 10 nm and 80 to 55 wt % of the polymer resin. For reference, the weight of the nano iridium oxide may be measured by a method, for example, thermogravimetric analysis. When the nano iridium oxide particles having a size of 1 to 10 nm are contained at less than 20 wt %, the electrical conductivity required by the hydrogen ion electrode may not be exhibited, and when the nano iridium oxide particles having a size of 1 to 10 nm are contained at more than 45 wt %, the physical stability of the hydrogen ion electrode may be decreased, and surface porosity may be increased, and therefore, the sensitivity may be reduced.

In an exemplary embodiment, the polymer resin is a moldable, thermoplastic and hydrophobic polymer resin having a glass transition temperature (Tg) of 20° C. or higher at which the polymer resin is dissolved in a water-soluble organic solvent, or a mixture of the polymer resins having the above properties. Such a resin may be, for example, a PMMA resin, a PVC resin, an ABS resin or a mixture thereof. The corresponding resins have a solid phase in a range of the glass transition temperature ($T_g$) or less at which the electrode is used.

In exemplary embodiments of the present invention, also, a pH sensor including a housing, the hydrogen ion electrode located in the housing and an electrical contact means connected to the hydrogen ion electrode is provided. The hydrogen ion electrode is in contact with a sample to become an electrode sensitive part. That is, the corresponding sensor has a composite material in which nano iridium oxide particles having a size of 1 to 10 nm and/or aggregates thereof are dispersed to be electrically connected in a moldable, thermoplastic and hydrophobic polymer matrix, thereby having electrical conductivity, and thus become an electrode sensitive part.

FIGS. 1 and 2 are schematic diagrams of a pH sensor including a hydrogen ion electrode according an exemplary embodiment of the present invention, where FIG. 1 is a schematic perspective view of the pH sensor and FIG. 2 is a schematic cross-sectional view of the pH sensor.

The hydrogen ion electrode 11 described above is molded in a cylindrical shape and in contact with a sample at one side to become an electrode sensitive part. At the other side of the hydrogen ion electrode, an electrical contact means 20, for example, a conductive metal wire or a metal rod is connected. Here, the electrical contact means 20 may be connected to the hydrogen ion electrode 11 via a conductive adhesive part 12 composed of a silver paste or a silver epoxy. The corresponding hydrogen ion electrode may be installed in a non-electrically conductive housing 30, for example, a plastic, to form a pH sensor. The housing 30 has an open part 31 at one side, and the electrode sensitive part, which is the hydrogen ion electrode 11, is exposed to a sample solution through the open part 31.

In the exemplary embodiments of the present invention, also, a method for manufacturing the hydrogen ion electrode composed of a composite material of nano iridium oxide and a polymer resin is provided, the method including: preparing a mixed solution of a moldable, thermoplastic and hydrophobic polymer resin, nano iridium oxide particles having a size of 1 to 10 nm and/or an aggregates thereof and a water-soluble organic solvent; obtaining a composite material of a polymer resin and nano iridium oxide by adding water to the mixed solution and removing the water-soluble organic solvent; and hot-molding the composite material.

According to such a manufacturing method, the electrode may be molded in various sizes and shapes at a lower temperature, compared to the pH electrode manufactured by conventional thermal decomposition, sputtering or high temperature sintering, and since a conductor, carbon black, requires no addition and dispersion processes, the electrode is very easily manufactured and has improved pH sensitivity and reproducibility, and low hysteresis. Also, although the manufactured hydrogen ion electrode does not include the conductor, carbon black, the hydrogen ion electrode can have the electrical conductivity required by the pH electrode due to the electrical conductivity of the nano iridium oxide particles.

In detail, first, the nano iridium oxide particles having a size of 1 to 10 nm and/or the aggregate, which are used in exemplary embodiments of the present invention may be synthesized by, for example, a synthesizing method from iridium precursors, or by adding commercially-available nano iridium oxide powder to distilled water and performing grinding and dispersing using ultrasonic waves.

The thermoplastic and hydrophobic polymer resin has to maintain physical strength at room temperature to be easily prepared. For this reason, a moldable, thermoplastic and hydrophobic polymer resin having a glass transition temperature ($T_g$) of 20° C. or higher or a mixture thereof may be used. Such a resin may be, for example, PMMA resin, PVC resin, ABS resin, or a mixture thereof. The corresponding resins have a solid phase in a temperature range at which electrodes having the glass transition temperature ($T_g$) or less are used.

The water-soluble organic solvent may be, for example, acetone, tetrahydrofuran (THF), dimethylformamide (DMF) or dimethylsulfoxide (DMSO).

Meanwhile, in the process of preparing the mixed solution, if needed to control the hardness of an electrode, a non-conductive and inactive micro powder such as titanium dioxide ($TiO_2$) may be further added without departing from the technical features of the present invention.

When preparing a mixed solution of the polymer resin, the prepared nano iridium oxide particles and/or aggregates thereof and a water-soluble organic solvent, a corresponding polymer resin medium may be dissolved in the water-soluble organic solvent and uniformly dispersed to prepare a mixed solution, and the nano iridium oxide particles and/or aggregates thereof may be mixed in the corresponding mixed solution and then uniformly dispersed.

Alternatively, the nano iridium oxide particles and/or aggregates thereof may be mixed with a water-soluble organic solvent and uniformly dispersed to prepare a mixed solution, and the polymer resin may be mixed in the mixed solution and allow the nano iridium oxide particles and/or aggregates thereof to be uniformly dispersed in the polymer resin medium.

Alternatively, a first mixed solution may be prepared by dissolving and uniformly dispersing the polymer resin in a water-soluble organic solvent, a second mixed solution may be prepared by mixing and uniformly dispersing nano iridium oxide particles and/or aggregates thereof in a water-soluble organic solvent, and then the first mixed solution and the second mixed solution may be mixed together to allow the nano iridium oxide particles and/or aggregates thereof to be uniformly dispersed in the polymer resin medium.

Subsequently, as excess water may be added to the mixed solution to remove a water-soluble organic solvent, the composite material of nano iridium oxide in which the nano iridium oxide particles and/or aggregates thereof are uniformly dispersed and the polymer resin may be separated (or precipitated) from the solvent.

Afterward, a hydrogen ion electrode material, which is the composite material of the electrically conductive nano iridium oxide and the polymer resin, is prepared by hot-molding the composite material with increased pressure. Here, the hot-molding with increased pressure may be conducted at a thermal decomposition temperature or less of the polymer medium used herein. Meanwhile, in an exemplary embodiment, the composite material may be ground to powder, and then hot-molded.

In an exemplary embodiment, a surface of the manufactured hydrogen ion electrode may be polished, and then stabilized in deionized water.

Thus, a hydrogen ion electrode (electrode sensitive part) 11 composed of the composite material may be formed by enclosing the hydrogen ion electrode material, which is the composite material of the nano iridium oxide and the polymer resin, molded as described above, at one end of a non-electrically conductive housing, for example, a non-conductive cylindrical plastic having an inner diameter the same as or larger than the diameter of the electrode material, an electrical contact means 20 such as a conductive metal wire or rod may be formed at the other end to make an electrical contact, and the corresponding electrical contact means 20 may be connected to a measuring device outside the housing 30. Also, a contact part 12 composed of conductive silver paste or silver epoxy may be further included between the hydrogen ion electrode 11 and the electrical contact means 20 (refer to FIGS. 1 and 2).

Alternatively, the electrode sensitive part composed of the composite hydrogen ion electrode material is formed by molding the composite hydrogen ion electrode material, fitting it in one end of the non-conductive plastic housing through hot molding and polishing the resultant material, and drilling a hole from the other end of the housing to the composite electrode material to make an electrical contact with it by means of a conductive metal wire or rod using conductive silver paste or silver epoxy to be connected to a measuring device.

Hereinafter, exemplary examples according to exemplary embodiments of the present invention will be described in detail. However, the present invention is not limited to the following examples, various forms of the examples can be implemented within the scope of the accompanying claims, and it will be understood to those of ordinary skill in the art that the following examples are merely provided to complete the disclosure of the present invention and to facilitate the practice of the present invention.

Example 1

Example for Preparing Nano Iridium Oxide

First, 2 g of $(NH_4)_2IrCl_6$ was added to a 500 ml round-bottom flask, 250 ml of deionized water was added to dissolve the $(NH_4)_2IrCl_6$, and then 0.1M NaOH was slowly added while stirring the resultant solution well with a magnetic stirrer to adjust pH to 8 to 9.

The round-bottom flask was equipped with a condenser, and the solution was shaken well and heated in a water bath at 95° C. for 30 minutes, and then cooled to room temperature.

The solution was changed into a solution containing suspended precipitate which had turned dark blue from brown. While the pH was measured again, 0.1M NaOH was added to adjust the pH to 8 to 9, and the solution was heated at 95° C. for 30 minutes and cooled to room temperature.

This procedure was repeated 6 to 7 times, the pH of the solution was fixed at 8 to 9, and 1 to 10 nm-sized nano iridium oxide particles and/or aggregates thereof formed in the solution were collected, washed and then resuspended in acetone.

FIGS. 3 and 4 are TEM images of nano iridium oxide particles or aggregates manufactured in an example of the present invention, where FIG. 3 is an enlarged image with a scale bar of 10 nm, and FIG. 4 is an enlarged image with a scale bar of 2 nm.

Meanwhile, instead of the above method, for example, nano iridium oxide particles may be prepared by a method as will be described below.

Modified Example for Preparing Nano Iridium Oxide 50 ml of distilled water was added to 1 g of commercial nano iridium oxide powder, ground and dispersed by sonication. To select nano iridium oxide having smaller particles, 300 ml of deionized water was added to the ground nano iridium oxide and dispersed further by sonication and magnetic stirring.

The iridium oxide aggregates having large particles were precipitated for about 10 seconds, and a nano iridium oxide supernatant that was not precipitated was transferred to a different beaker.

A dispersion in which the nano iridium oxide is dispersed was divided into centrifuge tubes, rotated at 3000 rpm for 15 minutes to precipitate the nano iridium oxide and remove a supernatant, thereby recovering the nano iridium oxide, and the nano iridium oxide was washed and then resuspended in acetone.

For reference, in the above-described process for preparing nano iridium oxide, a water-soluble organic solvent such as THF, DMF, DMSO, etc. can be used according to the solubility of the polymer, instead of acetone.

Preparation of Composite Material of Nano Iridium Oxide and Polymer Resin

A PMMA resin was put into a glass container into which acetone was added, and well stirred with a small magnetic bar to completely dissolve the polymer resin upon sealing, resulting in a polymer solution having a weight ratio of 25% (the preparation of a first mixed solution).

The nano iridium oxide prepared in the above-described example was added to acetone in a volume ratio of about 1:3, and uniformly dispersed (the preparation of a second mixed solution).

The first mixed solution was mixed with the second mixed solution so as to ensure that the weight ratio of the solid content of the nano iridium oxide and a polymer resin became 0.37:0.63, as measured by thermogravimetric analysis, and then the nano iridium oxide was stirred to be completely dispersed in the polymer solution using a vortex mixer.

The polymer solution in which the nano iridium oxide is dispersed was slowly added to excess water to remove a water-soluble solvent, acetone, from the polymer mixed material in which the nano iridium oxide is dispersed, and thus a solid was extracted. As a result, a composite material composed of the nano iridium oxide and the polymer resin was prepared. The composite material obtained by extraction as described above was dried and ground using a grinder.

Manufacture of Hydrogen Ion Electrode Consisting of Composite Material of Nano Iridium Oxide and Polymer Resin The prepared powder of the nano iridium oxide-PMMA polymer composite material was put into a mold having a diameter of 2 to 4 mm to be hot-molded at 150° C. with an increased pressure, thereby preparing a nano iridium oxide-polymer composite hydrogen ion electrode material having low electrical conductivity and a length of about 3 to 4 mm.

The hydrogen ion electrode material composed of the nano iridium oxide-polymer composite material was put into an end of a non-conductive cylindrical plastic having an inner diameter corresponding to the diameter of the electrode material, thereby forming an electrode sensitive part composed of the nano iridium oxide-polymer composite material, and a conductive metal wire or rod coated with a conductive silver paste was inserted to make an electrical contact and then fixed to its opening using an adhesive. The surface of the electrode sensitive part was smoothly polished with 2000-grit SiC sandpaper, and finally polished again using a 0.3 micrometer alumina abrasive. The electrode with polished sensing part was dipped into deionized water to hydrate, and therefore a stabilization process was performed.

Experimental Example

Confirmation of Sensitivity of Electrode

A sensitivity of the hydrogen ion electrode composed of the composite material of nano iridium oxide and a polymer resin (marked as electrode #29: containing 37% nano iridium oxide as measured by thermogravimetric analysis) was measured.

A commercial pH glass electrode was dipped into an universal buffer solution having a composition of 0.01 M phosphoric acid-boric acid-acetic acid-potassium chloride to adjust a pH of the solution to 3, and the electrode potential versus an Ag/AgCl (3.0 M KCl) reference electrode was measured while the pH was changed in a range of 3 to 11 by adding potassium hydroxide and nitric acid. The result is shown in FIG. 5. Here, the pH is increased to 11, and then repeatedly changed to 3 by adding nitric acid.

FIG. 5 is a graph showing a potential change according to the pH change of a hydrogen ion electrode composed of a composite material of nano iridium oxide and a polymer resin in an example of the present invention (reference electrode: Ag/AgCl), where the X axis is time (sec) and the Y axis is an electric potential (mV).

As shown in FIG. 5, it can be confirmed that the electrical potential of the electrode is rapidly stabilized into a new electrical potential according to pH change of the solution.

As shown on the right side of FIG. 5, after stepwise pH changing experiments were finished, the pH of the solution was abruptly adjusted to 11 again and measured. Then, it can be seen that, when the pH was changed back to 3, the electrode immediately sensed, and exhibited a hysteresis of about 1.7 mV, and then was stabilized.

Meanwhile, an electrical potential of the electrode according to each pH measured in FIG. 5 is shown in FIG. 5.

FIG. 6 is a graph showing the dependency of an electrode potential according to the pH change of a hydrogen ion electrode composed of a composite material of nano iridium oxide and a polymer, where the X axis is pH, and the Y axis is an electric potential (mV).

It was confirmed that the hydrogen ion electrode composed of the nano iridium oxide-polymer modified composite material according to exemplary embodiments of the present invention showed a slope of −59.7 mV/pH unit, which was very close to the theoretical value of −59.2 mV/pH unit.

Confirmation of Response of Electrode Signal

To check the response rate of the hydrogen ion electrode composed of the composite material of nano iridium oxide and polymer resin (marked as electrode #29: containing 37% nano iridium oxide as measured by thermogravimetric analysis), the pH of an 0.01M universal buffer solution was adjusted to 3.04, a predetermined amount of a 0.1M NaOH solution was rapidly added while the solution was well stirred, thereby changing the pH of the solution to 6.99 approximating 7, and then a response property of the electrode by time was recorded. Afterward, the pH of the solution was changed to 2.97 approximating 3 by adding a predetermined amount of 0.1M HCl, and changed again to 6.91 by adding 0.1M NaOH. Therefore, the result of recording the response property of the electrode according to time is shown in FIG. 7.

FIG. 7 is a graph showing a sensing time versus the pH change of a hydrogen ion electrode composed of a composite material of nano iridium oxide and a polymer in an example of the present invention, where the X axis is time (sec), and the Y axis is an electric potential (mV).

Conventionally, the response characteristic of the electrode signal was estimated as a time taken for the electrical potential of the electrode to reach 90% of a stable electrical potential value, $T_{90}$. However, in the experiment of confirming a response property of this example, a faster response was shown than time needed for mixing a 0.1 M HCl solution or a 0.1 M NaOH solution applied to the experiment, and thus it was not possible to estimate the precise $T_{90}$ value. This is because the pH electrodes of the exemplary embodiments of the present invention exhibit immediate sensitivity.

Confirmation of Surface Reproducibility of Electrode

FIG. 8 shows the results of the change in pH response sensitivity between the repeated polishing of the electrode surface. The electrode surface (marked as electrode #29: containing 37% nano iridium oxide as measured by thermogravimetric analysis) was grinded with 2000-grit SiC sandpaper, polished with an 0.3-micrometer alumina abrasive, dipped into deionized water to stabilize, and then the pH response sensitivities in the solutions of pH 4, 7 and 10 e were measured eight times.

FIG. 8 is a graph showing the reproducibility of the hydrogen ion sensitivity slope according to the polishing of a surface of a hydrogen ion electrode composed of a composite material of nano iridium oxide and a polymer according to an example of the present invention, where the X axis is a measurement number, and the Y axis is a hydrogen ion sensitivity slope (mV/pH).

As seen from FIG. 8, an average slope (mV/pH unit) of the pH sensitivity was −58.12 mV/pH unit, and an excellent relative standard deviation (rsd) of 0.5% was shown.

Confirmation of Reproducibility of Sensitivity of Electrode

FIG. 9 shows the changes in sensitivity of the electrode due to a long-term use of the hydrogen ion electrode composed of the composite material of nano iridium oxide and a polymer resin (referred to as electrode #29: containing 37% of nano iridium oxide).

FIG. 9 is a graph showing stability over time of a hydrogen ion sensitivity slope of a hydrogen ion electrode composed of a composite material of nano iridium oxide and a polymer in an example of the present invention, where the X axis is a measuring day, and the Y axis is a hydrogen ion sensitivity slope (mV/pH).

In FIG. 9, potentials of the electrode were repetitively measured at pH 4, 7, and 10 for 26 days, and the electrode sensitivity slope calculated from the results was shown together. The electrode was stored in distilled water after daily measurement. From the analytical results of FIG. 9, the electrode sensitivity, the average slope, was −58.44 mV/pH, the rsd was 0.91%, and thus a very high reproducibility of sensitivity was confirmed for a long period of time.

Also, after one month of the initial use, an average value of the pH sensitivity slope calculated from the potentials measured on the hydrogen ion electrode composed of the composite material (marked as electrode #29: containing 37% nano iridium oxide as measured by thermogravimetric analysis) 20 times in buffer solutions with pH 4, 7, and 10 was −58.69 mV/pH unit, the rsd of the slope was 0.44%, and thus stable and reproducible pH sensitivity was confirmed.

As described above, in the hydrogen ion electrode according to the exemplary embodiments of the present invention, the nano iridium oxide aggregates are dispersed in the polymer resin matrix, and thus the pH sensitivity of the electrode surface exposed to a sample solution may be very fast and close to the theoretical value. Also, particularly, the hydrogen ion electrode may have high reproducibility in the fast and near-theoretical in the sensitivity, and despite abrupt pH change and repetitive use, may have a very low hysteresis of 1 to 2 mV. Also, since the hydrogen ion electrode can have durability in accordance with high physical strength and allow its surface to be regenerated reproducibly by simple polishing when fouled or deactivated, the lifetime of the hydrogen ion electrode can be greatly extended until the hydrogen ion electrode material composed of the composite material is exhausted.

INDUSTRIAL APPLICABILITY

The present invention relates to a hydrogen ion electrode composed of a composite material of nano iridium oxide and a polymer resin and enabling regeneration of a surface by surface polishing, a pH sensor using the same, and a method for manufacturing the same. The corresponding hydrogen ion electrode can be useful to detect pH in water quality monitoring systems or on-line detecting systems, which monitor the concentration of hydrogen ions in a solution for a long period of time, or of a sample causing severe fouling on the sensor surface, for example, food, soil, waste, or bio-samples, while the surface is regenerated by polishing.

The invention claimed is:

1. A hydrogen ion electrode composed of a composite material of nano iridium oxide and a polymer resin and enabling surface regeneration, in which nano iridium oxide particles having a size of 1 to 10 nm are dispersed to be electrically connected in a moldable, thermoplastic and hydrophobic polymer resin matrix in an individual particle state, an aggregate state in which the particles agglomerate, or a state in which the individual particles and the aggregates are mixed to allow electrical conduction of the hydrogen ion electrode.

2. The hydrogen ion electrode of claim 1, wherein the nano iridium oxide particles having a size of 1 to 10 nm are dispersed in an individual particle state, the individual particles being electrically connected so as to allow electrical conduction of the hydrogen ion electrode.

3. The hydrogen ion electrode of claim 1, wherein the nano iridium oxide particles having a size of 1 to 10 nm are dispersed in an aggregate state, the aggregates being electrically connected so as to allow electrical conduction of the hydrogen ion electrode.

4. The hydrogen ion electrode of claim 1, wherein the nano iridium oxide particles having a size of 1 to 10 nm are dispersed in a state in which individual particles and aggregates are mixed, the particles or aggregates being electrically connected so as to allow electrical conduction of the hydrogen ion electrode.

5. The hydrogen ion electrode of claim 1, wherein the hydrogen ion electrode has a hysteresis potential of 1 to 2 mV according to pH change in which the pH is increased from 3 to 11 and then decreased to 3.

6. The hydrogen ion electrode of claim 1, which contains 20 to 45 wt % of the nano iridium oxide particles and 80 to 55 wt % of the polymer resin.

7. The hydrogen ion electrode of claim 1, wherein the polymer resin is a polymer resin having a glass transition temperature ($T_g$) of 20° C. or more, or a mixture thereof.

8. A pH sensor, comprising:
a non-electrically conductive housing;
the hydrogen ion electrode of claim 1, located in the housing; and
an electrical contact means connected to the hydrogen ion electrode.

9. The pH sensor of claim 8, wherein the housing is a cylindrical housing having an open part through which the hydrogen ion electrode is exposed at one side, and the electrical contact means is connected to an outside of the cylindrical housing at the other side.

10. A method for manufacturing a hydrogen ion electrode composed of a composite material of nano iridium oxide and a polymer resin, comprising:

preparing a mixed solution composed of a moldable, thermoplastic and hydrophobic polymer resin, one or more selected from the group consisting of nano iridium oxide particles having a size of 1 to 10 nm and aggregates in which the nano iridium oxide particles agglomerate, and a water-soluble organic solvent;
obtaining a composite material of a polymer resin and nano iridium oxide by adding water to the mixed solution and removing the water-soluble organic solvent; and
manufacturing a hydrogen ion electrode by hot-molding the composite material.

11. The method of claim 10, wherein, in the preparation of the mixed solution, a first mixed solution is prepared by dissolving and dispersing the polymer resin in a water-soluble organic solvent, a second mixed solution is prepared by mixing one or more of the nano iridium oxide particles and aggregates with the water-soluble organic solvent and dispersing them, and the first mixed solution and the second mixed solution are mixed and dispersed.

12. The method of claim 10, wherein the hydrogen ion electrode is manufactured by grinding the composite material into a powder and hot-molding the powder.

13. The method of claim 10, wherein the surface of the manufactured hydrogen ion electrode is polished and stabilized in water.

14. The method of claim 10, further comprising:
equipping the hot-molded hydrogen ion electrode in a non-electrically conductive housing, and connecting an electrical contact means to the hydrogen ion electrode.

* * * * *